United States Patent

Holton et al.

[11] Patent Number: 5,350,866
[45] Date of Patent: * Sep. 27, 1994

[54] 10-DESACETOXYTAXOL DERIVATIVES

[75] Inventors: Robert A. Holton, Tallahassee, Fla.; Shu-Hui Chen, New Haven; Vittorio Farina, West Hartford, both of Conn.

[73] Assignees: Bristol-Myers Squibb Company, New York, N.Y.; Florida State University, Tallahassee, Fla.

[*] Notice: The portion of the term of this patent subsequent to Sep. 26, 2010 has been disclaimed.

[21] Appl. No.: 949,449

[22] Filed: Sep. 22, 1992

Related U.S. Application Data

[63] Continuation-in-part of Ser. No. 863,849, Apr. 6, 1992, abandoned, which is a continuation-in-part of Ser. No. 763,805, Sep. 23, 1991, abandoned, which is a continuation-in-part of Ser. No. 900,408, Jun. 18, 1992, abandoned.

[51] Int. Cl.$^5$ ............................................. C07D 305/14
[52] U.S. Cl. ............................. 549/510; 549/511
[58] Field of Search ............................. 549/510, 511

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,924,011 | 5/1990 | Denis et al. | 849/510 |
| 4,924,012 | 5/1990 | Colin et al. | 849/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,136,060 | 8/1992 | Holton | 549/510 |
| 5,248,796 | 9/1993 | Chen et al. | 549/510 |

FOREIGN PATENT DOCUMENTS

| | | |
|---|---|---|
| 253738 | 7/1987 | European Pat. Off. . |
| 253739 | 7/1987 | European Pat. Off. . |
| 336840 | 4/1989 | European Pat. Off. . |
| 336841 | 4/1989 | European Pat. Off. . |
| 247378 | 9/1990 | European Pat. Off. . |

OTHER PUBLICATIONS

Denis and Greene, "A Highly Efficient, Practical Approach to Natural Taxol", J. Am. Chem. Soc. 1988, 110, 5917–5919.

Holton et al., "A Synthesis of Taxusin", J. Am. Chem. Soc., 1988, 110, pp. 6558–6560.

Holton, "Synthesis of the Taxane Ring System", J. Am. Chem. Soc., 1984, 106, pp. 5731–5732.

(List continued on next page.)

Primary Examiner—Bernard Dentz
Assistant Examiner—Ba K. Trinh
Attorney, Agent, or Firm—Senniger, Powers, Leavitt & Roedel

[57] ABSTRACT

The present invention relates to 10-desacetoxytaxol and derivatives thereof, which are useful as antitumor agents. These compounds have the formula

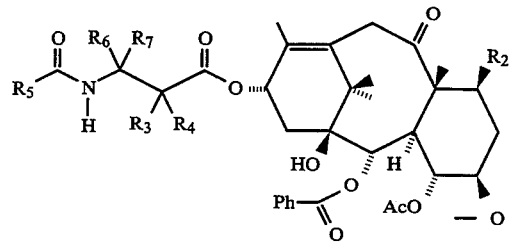

wherein $R_2$ is hydrogen, hydroxy or a protected hydroxy group; $R_3$ and $R_4$ are independently hydrogen, hydroxy, a protected hydroxy group, methyl, —SH, —$NH_2$, or —$NR_8R_9$; $R_5$ is $R_{10}$, or —$OR_{10}$; $R_6$ and $R_7$ are independently hydrogen, alkyl, or aryl; $R_8$ and $R_9$ are independently hydrogen, alkyl, alkenyl, alkynyl, or aryl; and $R_{10}$ is alkoxy, alkyl, alkenyl, alkynl, or aryl.

20 Claims, No Drawings

OTHER PUBLICATIONS

Mukerjee et al., "β–Lactams: Retrospect and Prospect", Tetrahedron vol. 34, Report No. 52, pp. 1731–1767 (1978).

Wani et al., "Plant Antitumor Agents, VI. The Isolation and Structure of Taxol, a Novel Antileukemic and Antitumor Agent from Taxus Brevifolia", J. Am. Chem. Soc. 93:9, May 5, 1971, pp. 2325–2327.

Samaranayake et al., "Modified Taxols. 5.1 Reaction of Taxol with Electrophilic Reagents and Preparation of a Rearranged Taxol Derivative with Tubulin Assembly Activity 3.", J. Org. Chem. 1991, 56, 5114–5119.

Kaiser et al., "Synthesis of Esters of Acid–Unstable Alcohols by Means of n–butyllithium", J. Org. Chem., 1970, 35, 1198.

Ojima et al., "New and Efficient Approaches to the Semisynthesis of Taxol and its C–13 Side Chain Analogs by Means of β–Lactam Synthon Method", Tetrahedron vol. 48, No. 34, pp. 6985–7012, 1992.

10-DESACETOXYTAXOL DERIVATIVES

REFERENCE TO RELATED APPLICATIONS

This application is a continuation-in-part of U.S. application Ser. No. 07/863,849, filed Apr. 6, 1992 now abandoned, which in turn is a continuation-in-part of U.S. application Ser. No. 07/763,805, filed Sep. 23, 1991, now abandoned, and this application is a continuation-in-part of U.S. application Ser. No. 07/900,408, filed Jun. 18, 1992 now abandoned.

BACKGROUND OF THE INVENTION

The present invention relates to novel antitumor agents. More particularly, the present invention relates to 10-desacetoxytaxol and derivatives thereof.

Taxol is a natural product extracted from the bark of yew trees. It has been shown to have excellent antitumor activity in vivo animal models, and recent studies have elucidated its unique mode of action, which involves abnormal polymerization of tubulin and disruption of mitosis. It is currently undergoing clinical trials against ovarian, breast and other types of cancer in the United States and France and preliminary results have confirmed it as a most promising chemotherapeutic agent. The structure of taxol and the numbering system conventionally used is shown below; this numbering system is also applicable to compounds of the present invention.

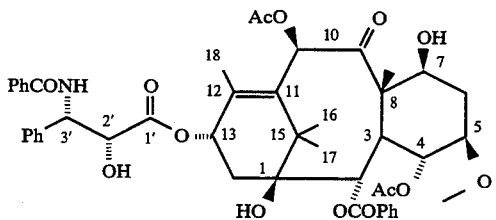

SUMMARY OF THE INVENTION

Among the objects of the present invention, therefore, is the provision of the novel taxane, 10-desacetoxytaxol, and derivatives thereof, which exhibit antitumor activity.

In accordance with the present invention, a compound is provided having the following structural formula (1):

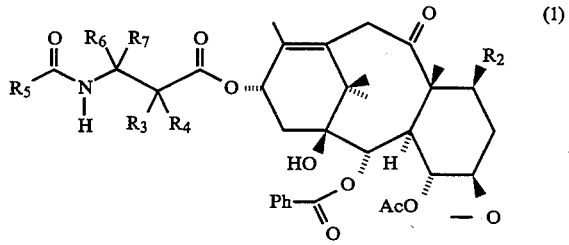

wherein $R_2$ is hydrogen, hydroxy or a protected hydroxy group; $R_3$ and $R_4$ are independently hydrogen, hydroxy, a protected hydroxy group, methyl, —SH, —NH$_2$, or —NR$_8$R$_9$; $R_5$ is $R_{10}$, or —OR$_{10}$; $R_6$ and $R_7$ are independently hydrogen, alkyl, or aryl; $R_8$ and $R_9$ are independently hydrogen, alkyl, alkenyl, alkynyl, or aryl; and $R_{10}$ is alkoxy, alkyl, alkenyl, alkynl, or aryl.

Also provided are the compounds 10-desacetoxytaxol and 10-deoxytaxotere.

Other objects and features of this invention will be in part apparent and in part pointed out hereinafter.

DETAILED DESCRIPTION OF THE INVENTION

As used herein "Ar" means aryl; "Ph" means phenyl; "Ac" means acetyl; "R" means alkyl; "11-ene" means a double bond between carbon atoms 11 and 12 of a compound of formula (1); and "10,12-diene" means double bonds between carbon atoms 10 and 11, and 12 and 18 of a compound of formula (1). "Hydroxy protecting group" includes, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloroethyl; alkenyl carbonates having from two to six carbon atoms such as vinyl and allyl; cycloalkyl carbonates have from three to six carbon atoms such as cyclopropyl, cyclobutyl, cyclopentyl and cyclohexyl; and phenyl or benzyl carbonates optionally substituted on the ring with one or more C$_{1-6}$alkoxy, or nitro.

The present invention provides novel 10-desacetoxytaxol derivatives of the formula (1)

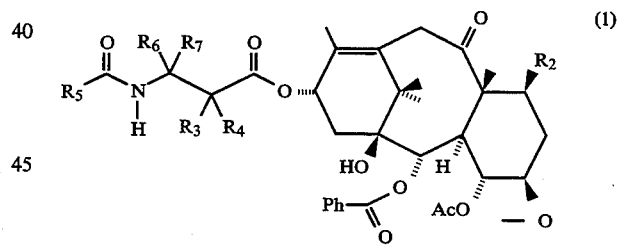

wherein $R_2$ is hydrogen, hydroxy or a protected hydroxy group; $R_3$ and $R_4$ are independently hydrogen, hydroxy, a protected hydroxy group, methyl, —SH, —NH$_2$, or —NR$_8$R$_9$; $R_5$ is $R_{10}$, or —OR$_{10}$; $R_6$ and $R_7$ are independently hydrogen, alkyl, or aryl; $R_8$ and $R_9$ are independently hydrogen, alkyl, alkenyl, alkynyl, or aryl; and $R_{10}$ is alkoxy, alkyl, alkenyl, alkynl, or aryl.

Exemplary compounds within the generic formula are depicted hereinbelow:

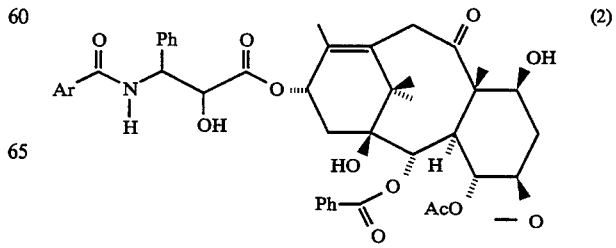

3
-continued

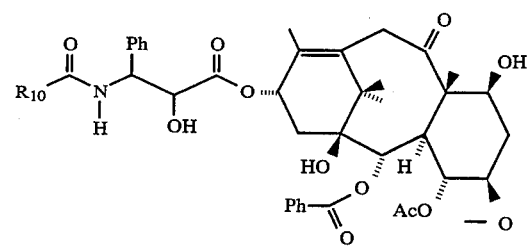 (3)

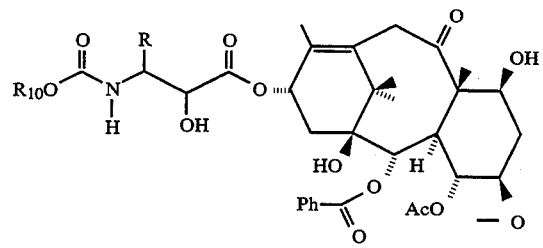 (4)

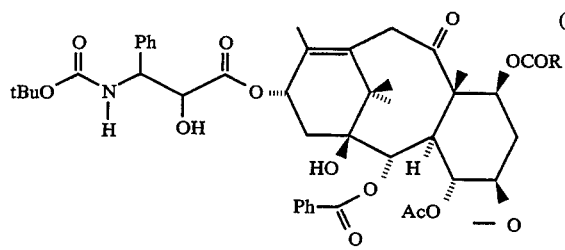 (5)

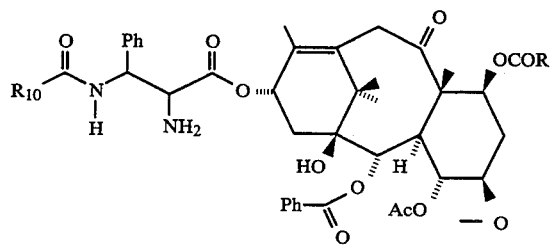 (6)

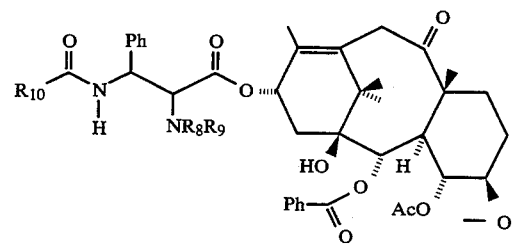 (7)

4
-continued

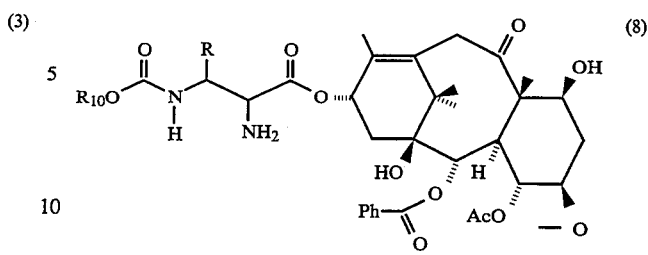 (8)

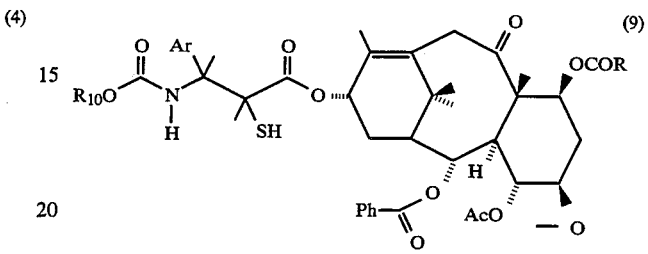 (9)

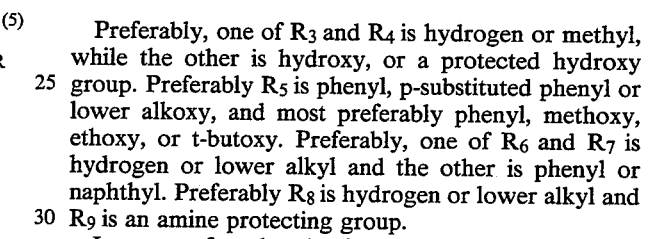

Preferably, one of $R_3$ and $R_4$ is hydrogen or methyl, while the other is hydroxy, or a protected hydroxy group. Preferably $R_5$ is phenyl, p-substituted phenyl or lower alkoxy, and most preferably phenyl, methoxy, ethoxy, or t-butoxy. Preferably, one of $R_6$ and $R_7$ is hydrogen or lower alkyl and the other is phenyl or naphthyl. Preferably $R_8$ is hydrogen or lower alkyl and $R_9$ is an amine protecting group.

In one preferred embodiment of compounds of formula (1), $R_2$ is hydroxy or a protected hydroxy group; $R_3$ is hydrogen; $R_4$ is hydroxy or a protected hydroxy group; $R_5$ is phenyl; $R_6$ is hydrogen and $R_7$ is phenyl. In another preferred embodiment, $R_5$ is t-butoxy. Where either $R_3$ or $R_4$ is a protected hydroxy group, it is preferably one of the carbonate type, most preferably it is selected from the group consisting of 2,2,2-trichloroethoxycarbonyl, allyloxycarbonyl, and benzyloxycarbonyl; or one of the trialkylsilyl type, most preferably triethylsilyl. The most preferred embodiments of compounds of formula (1) are: 1) 10-desacetoxytaxol; and 2) 10-deoxytaxotere.

A method for preparing compounds of formula (1) is provided by following the reaction sequence depicted in Scheme I.

SCHEME I

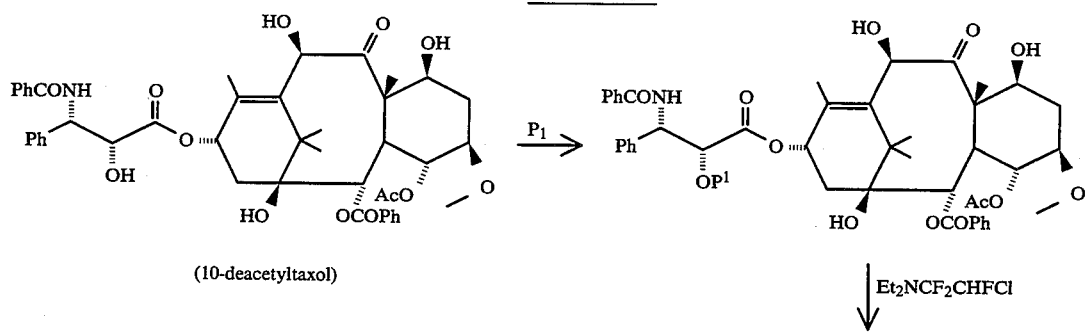

-continued
SCHEME I

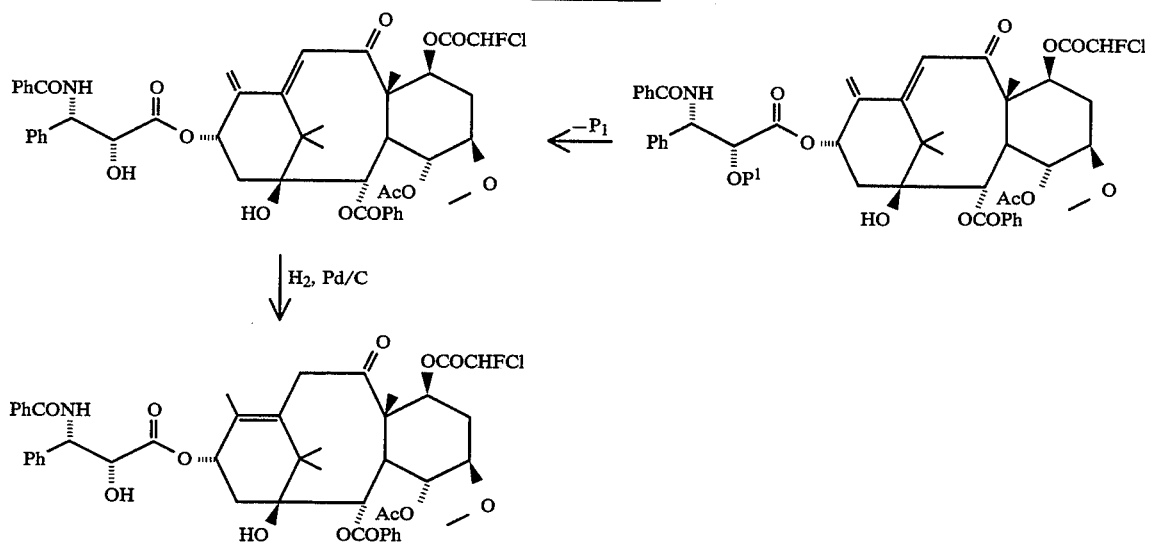

As illustrated, the starting materials used for the preparation of compounds of formula (1) using Scheme 1 include 10-deacetyltaxol, which may be obtained from taxol by treating the latter with zinc bromide in chloroform/methanol as reported in G. Samaranayake et al., *J. Org. Chem.*, 1991, 56:5114–5119, hereby incorporated by reference.

In Scheme I, $P_1$ is a hydroxy protecting group. Thus in the first reaction step, the 2'-hydroxy group of 10-deacetyltaxol is protected; the protecting group may be one that can be introduced and removed without unacceptably affecting the rest of the molecule, more preferably it may be one that preferentially blocks the 2'-hydroxy group over the two secondary hydroxy groups oil the ring, namely, the 7- and 10-hydroxy groups. Protection of a hydroxy group may be accomplished by methods well known in the art; for example, reacting with a carboxylic acid or its acylating equivalent to form an ester, reacting with an alkyl halide in the presence of a base to form an ether, or reacting with a chloroformate to form the carbonate.

The preferred 2'-hydroxy protecting group in this reaction is a carbonate which can be formed by treating 10-deacetyltaxol with an appropriate chloroformate, for example, allyl or benzyl chloroformate to form the corresponding carbonate. The reaction is carried out in an inert organic solvent such as dichloromethane, tetrahydrofuran, acetonitrile, dimethylformamide, benzene, pyridine, p-dioxan, and preferably in the presence of an acid scavenger such as an amine base, for example, pyridine, diisopropylethylamine, 4-aminopyridine, triethylamine and the like, or an inorganic base such as potassium carbonate or tetrabutylammonium hydroxide, at a suitable temperature which may be −78° C. to about 50° C., depending on the particular reagents chosen. Generally from about one to ten equivalents of the protecting group reagent relative to the taxol compound may be used; it is advantageous to monitor the reaction for example by thin-layer chromatography so as to achieve the desired degree of protection.

The 2'-hydroxy protected 10-deacetyltaxol thus obtained is then treated with 1,1,2-trifluoro-2-chlorotriethylamine (hereinafter TFCT) to give 2'-hydroxy protected 7-O-chlorofluoroacetyl-10-desacetoxy-11,12-dihydrotaxol-10,12(18)-diene. TFCT can be prepared from diethylamine and trifluorochloroethylene according to the method reported in N. N. Yarovenko, *J. Org. Chem. USSR* (English), 1959, 29:2125-8, hereby incorporated by reference. The reaction of 2'-hydroxy protected 10-deacetyltaxol and TFCT is carried out in an inert organic solvent such as halogenated hydrocarbons, for example, dichloromethane, chloroform, and carbon tetrachloride, at a temperature of from about 0° C. up to the refluxing temperature of the reaction solution, preferably the reaction is run at ambient temperature. The TFCT is used in at least 1 equivalent to the taxol reactant, but preferably it is used in excess; typically from about one to about ten equivalents of TFCT may be used relative to the taxol reactant.

The 2'-hydroxy protecting group can be removed using methods known in the art that are suitable for the particular protecting group used; for example, acid or base catalyzed hydrolysis, reduction, hydrogenolysis, and the like. Thus the allyl carbonate can be removed by tributyltin hydride and tetrakis(triphenylphosphine)-palladium; the benzyl carbonate can be removed by catalytic hydrogenolysis.

7-O-Chlorofluoroacetyl-10-desacetoxy-11,12-dihydrotaxol-10,12(18)-diene can be converted to 10-desacetoxy-7-O-chlorofluoroacetyltaxol by catalytic hydrogenation in which the catalyst may be, for example, palladium, platinum, rhodium and the like. In cases where the 2'-hydroxy protecting group used in the previous steps of the reaction sequence is benzyloxycarbonyl, catalytic hydrogenation converts the 10,12-diene into the 11-ene, and removes the 2'-protecting group in one step. It is understood that the order of deprotecting the 2'-hydroxy group and hydrogenation is not crucial, and either may be effected prior to the other.

A further method for preparing compounds of the present invention provides compounds of formula (1) wherein $R_2$ is hydrogen, hydroxy, or protected hydroxy; and $R_5$ is phenyl. Compounds of this type may be prepared from 10-deacetyltaxol or 10-deacetyl-7-epitaxol as depicted in Scheme II.

SCHEME II

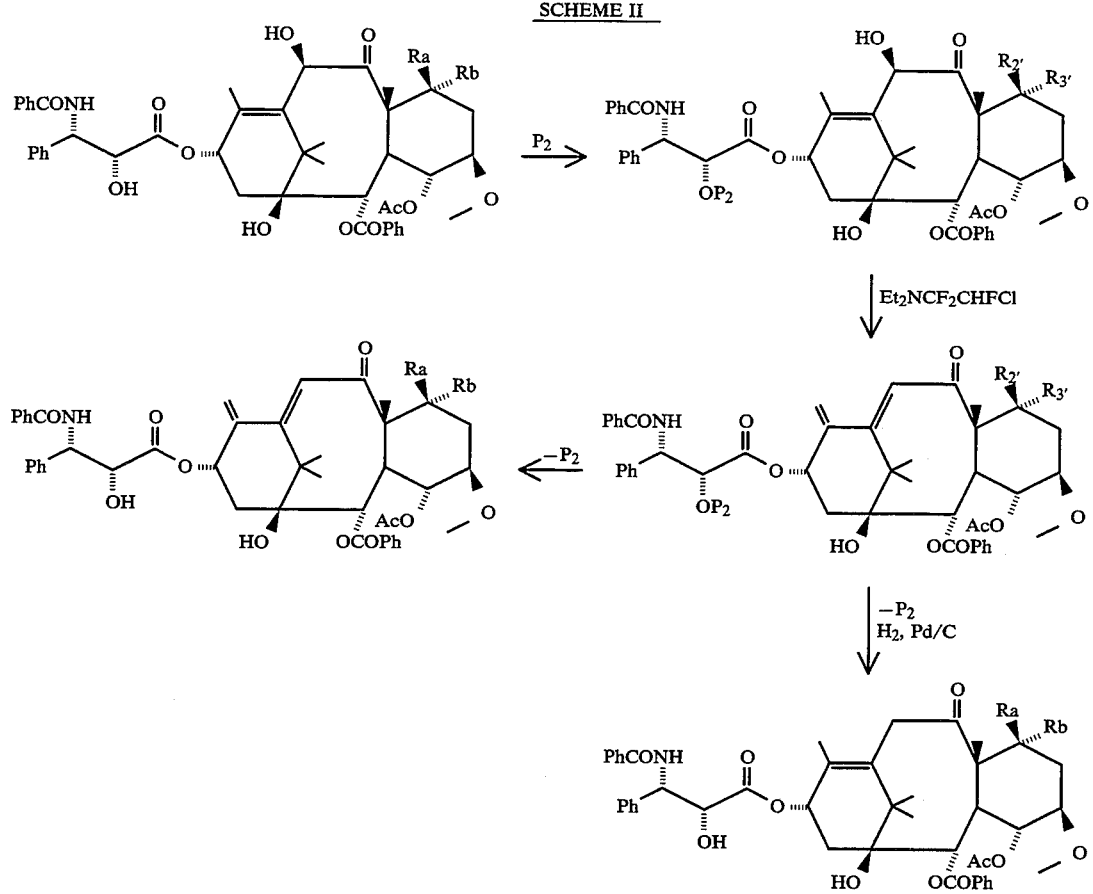

In Scheme II, $R_a$ is hydroxy, $R_b$ is hydrogen, $R_2$, is $OP_2$, and $R_3$, is hydrogen; or $R_a$ is hydrogen, $R_b$ is hydroxy, $R_2$, is hydrogen, and $R_3$, is hydroxy; $P_2$ is a hydroxy protecting group. When 10-deacetyltaxol (i.e. $R_a$ is hydroxy and $R_b$ is hydrogen) is the starting material, it is desirable to protect both the 2'- and the 7-hydroxy groups, and that the 10-hydroxy group be left free; preferably the protecting group is 2,2,2-trichloroethoxycarbonyl which can be introduced by reacting the taxol reactant with 2,2,2-trichloroethyl chloroformate in the presence of a base such as pyridine, diisopropylamine, triethylamine, dimethylaminopyridine, and the like. To control the degree of protection and to minimize blocking the 10-hydroxy group, the base is usually used in about one to two equivalents relative to taxol and the chloroformate in about 0.6 to about 1.5 equivalents relative to taxol. When 10-deacetyl-7-epitaxol (i.e. $R_a$ is hydrogen and $R_b$ is hydroxy) is the starting material, only the 2'-hydroxy group is protected since the 7-hydroxy group is substantially more inert than the 2'-hydroxy group, and is relatively insusceptible to acylation, either with a chloroformate, or with the TFCT in the subsequent step.

The 2',7-bishydroxy protected 10-deacetyltaxol or 2'-hydroxy protected 10-deacetyl-7-epitaxol thus obtained is then treated with TFCT to give 2',7-bishydroxy protected 10-desacetoxy-11,12-dihydrotaxol-10,12(18)-diene or 2'-protected 10-desacetoxy-11,12-dihydro-7-epitaxol-10,12(18)-diene, respectively. The reaction with TFCT is carried out in an inert organic solvent such as halogenated hydrocarbons such as dichloromethane, chloroform and carbon tetrachloride, at a temperature of from about 0° C. to about the refluxing temperature of time reaction solution, preferably the reaction is run at ambient temperature. The TFCT is used in at least 1 equivalent to the taxol reactant, but preferably it is used in excess; typically TFCT is used from about one to about ten equivalents. The 2'- and, if present, the 7-hydroxy protecting group is then removed using a method suitable for the particular protecting group to provide 10-desacetoxy-11,12-dihydrotaxol-10,12(18)-diene or 10-desacetoxy-11,12-dihydro-7-epitaxol-10,12(18)-diene; for example, trichloroethyoxycarbonyl group is removed by a zinc reagent, benzyloxycarbonyl is removed by hydrogenolysis, and allyl carbonate is removed by tributyltin hydride and tetrakis(triphenylphosphine)palladium. 10-Desacetoxy-11,12-dihydrotaxol-10,12(18)-diene and 10-desacetoxy-11,12-didehydro-7-epitaxol-10,12(18)-diene may then be subjected to catalytic hydrogenation as previously discussed to provide 10-desacetoxytaxol and 10-desacetoxy-7-epitaxol, respectively.

2',7-Bishydroxy protected 10-desacetoxy-11,12-dihydrotaxol-10,12(18)-diene or 2'-hydroxy protected 10-desacetoxy-11,12-dihydro-7-epitaxol-10,12 (18)-diene can also be subjected to catalytic hydrogenation to give 2',7-bishydroxy protected 10-desacetoxytaxol or 2'-hydroxy protected 10-desacetoxy-7-epitaxol, respectively. The hydroxy protecting groups may be removed as previously described to provide 10-desacetoxytaxol or 10-desacetoxy-7-epitaxol.

A further method for preparing compounds of the present invention provides compounds of formula (1) wherein $R_2$ is hydroxy or a protected hydroxy group, $R_3$ is hydrogen; $R_4$ is hydrogen, hydroxy, or a hydroxy protecting group; $R_5$ is t-butoxy; $R_6$ is hydrogen and $R_7$ is phenyl. Compounds of this type may be prepared from 7-protected 10-desacetoxy baccatin III or 10-desacetoxy-7-epi-baccatin III using the process shown in Scheme III.

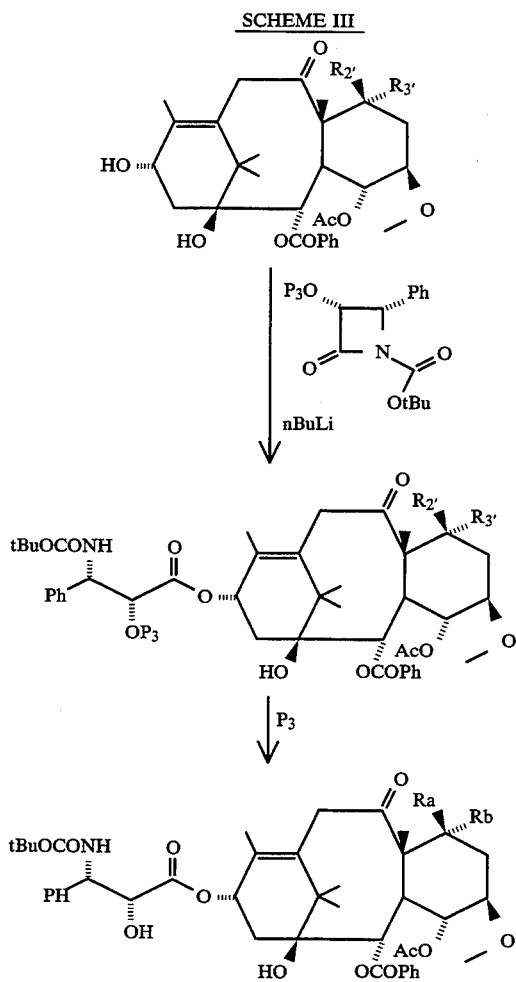

In Scheme III, $R_a$ is hydroxy, $R_b$ is hydrogen, $R_2$, is —$OP_3$, and $R_3$, is hydrogen; or $R_a$ is hydrogen, $R_b$ is hydroxy, $R_2$, is hydrogen, and $R_3$, is hydroxy; $P_3$ is a hydroxy protecting group; preferably it is a trialkylsilyl group, most preferably triethylsilyl. 7-Hydroxy protected 10-desacetoxy baccatin III or 10-desacetoxy-7-epi-baccatin III is treated with a strong base such as n-butyl lithium to generate the corresponding 13-alkoxide. The alkoxide is reacted with (3R,4S)-1-t-butoxycarbonyl-4-phenyl-3-protected hydroxy-2-azetidinone in an inert organic solvent such as tetrahydrofuran to provide the corresponding 2′,7-bishydroxy protected 10-deoxytaxotere. The reaction is carried out at a low temperature in the range of about $-20°$ C. to about $25°$ C., preferably at about $0°$ C. The hydroxy protecting groups are then removed to provide 10-deoxytaxotere using conventional methods, for example triethylsilyl group may be removed by acid hydrolysis with hydrochloric acid.

The reaction sequence depicted in Scheme III shows the preparation of 10-deoxytaxotere or 10-deoxy-7-epitaxotere; however, it is equally applicable for preparing 10-desacetoxytaxol or 10-desacetoxy-7-epitaxol. Thus, 10-desacetoxytaxol and 10-desacetoxy-7-epitaxol may be obtained in an analogous manner by replacing the β-lactam shown in Scheme III with (3R,4S)-1-benzoyl-4-phenyl-3-hydroxy protected-2-azetidinone.

Other derivatives of 10-desacetoxytaxol within the scope of formula (1) may readily be prepared by selection of the proper substituents for the β-lactam which forms the β-amido ester side chain at C-13 of the taxol structure.

10-Desacetoxybaccatin III and 10-desacetoxy-7-epibaccatin III may be obtained from 10-deacetylbaccatin III and 10-deacetyl-7-epibaccatin III by the process shown in Scheme IV.

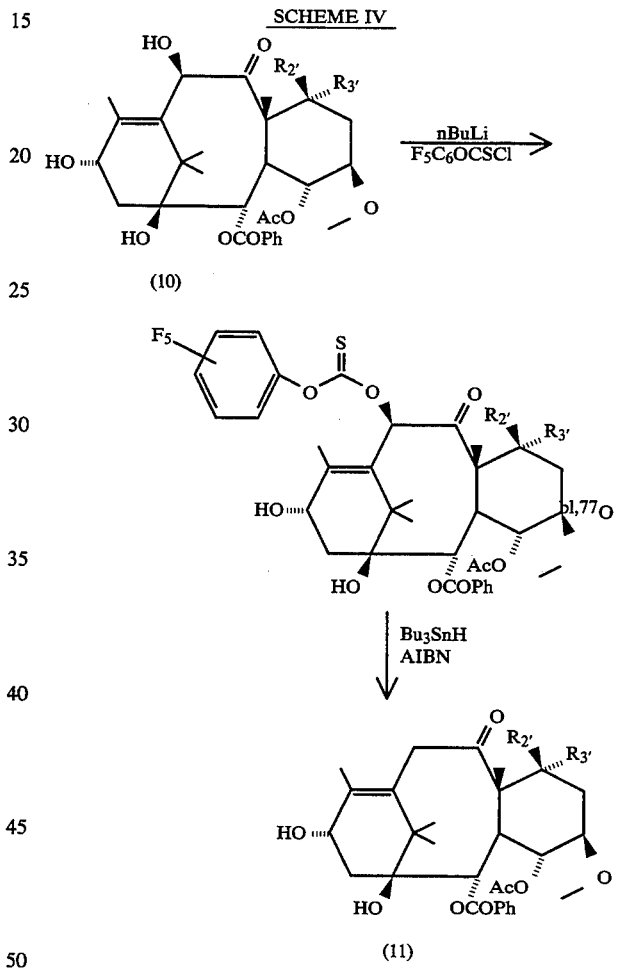

In Scheme IV, $R_2$, is hydrogen and $R_3$, is hydroxy, or $R_2$, is protected hydroxy and $R_3$, is hydrogen. Preferably, the hydroxy protecting group is trialkylsilyl ether type, for example, triethylsilyl. Thus 10-deacetylbaccatin III is first treated with a strong base such as n-butyl lithium, and alkoxide generated in situ is reacted with pentafluorophenyl chlorothionoformate to provide the corresponding 10-(pentafluorophenyl)thiocarbonate. The reaction is carried out in an inert organic solvent such as tetrahydrofuran, at a temperature in the range of about $-78°$ C. to about room temperature. The thiocarbonate thus obtained is treated with a suitable reagent such as tributyltin hydride, triphenyltin hydride, trimethylsilane, and tributyltinchloride and sodium cyanoborohydride, in the presence of a radical initiator such as azobisisobutyronitrile (AIBN). The reaction is carried out in an organic solvent such as t-butanol, N- methylpyrrolidone, dimethylsulfoxide, dimethylformamide, toluene and benzene at a temperature from about 80° C. to about 115° C. to provide 7-protected hydroxy-10-desacetoxy baccatin III or 7-epibaccatin III. Alternatively, the reaction can be carried out under photochemical conditions (triorganotin hydride, hv, benzene, 0° C.-room temperature). The hydroxy protecting group may be removed using methods known in the art; for example, triethylsilyl can be removed by acid hydrolysis using hydrochloric acid.

The 10-desacetoxytaxol derivatives of the present invention are useful agents for inhibiting tumor growth in animals and human. Compounds were evaluated in in vitro cytoxicity activity against human colon carcinoma cells HCT-116 and HCT-116/VM46. The HCT116/VM cells are cells that have been selected for teniposide resistance and express the multidrug resistance phenotype, including resistance to taxol. Cytotoxicity was assessed in HCT-116 human colon carcinoma cells by XTT (2,3-bis(2-methoxy-4-nitro-5-sulfophenyl)-5-[(phenylamino)carbonyl]2H-tetrazolium hydroxide) assay as reported in D. A. Scudiero, et al., "Evaluation of soluble tetrazolium/formazan assay for cell growth and drug sensitivity in culture using human and other tumor cell lines, "Cancer Res. 48:4827–4833, 1988. Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance, the greater the number of live cells. The results are expressed as an $IC_{50}$, which is the drug concentration required to inhibit cell proliferation (i.e., absorbance at 450 nm) to 50% of that of untreated control cells. The $IC_{50}$ values for 10-desacetoxytaxol and taxol are given in Table I.

TABLE I

| In vitro cytotoxicity for taxol analogs against human colon carcinoma cells. | | |
|---|---|---|
| | $IC_{50}$ (μM) | |
| Compound | HCT-116 | HCT-116/VM46 |
| 10-Desacetoxytaxol | 0.008 | 1.22  (153) |
| Taxol | 0.004 | 0.440 (124) |

*Value in parenthesis is fold resistance relative to HCT-116 cells.

Compounds of formula (1) of the instant invention are useful for inhibiting tumor growth in animals including humans and are preferably administered in the form of a pharmaceutical composition comprising an effective antitumor amount of compound of the instant invention in combination with a pharmaceutically acceptable carrier or diluent.

Antitumor compositions herein may be made up in any suitable form appropriate for desired use; e.g., oral, parenteral or topical administration. Examples of parenteral administration are intramuscular, intravenous, intraperitoneal, rectal and subcutaneous administration.

The diluent or carrier ingredients should not be such as to diminish the therapeutic effects of the antitumor compounds.

Suitable dosage forms for oral use include tablets, dispersible powders, granules, capsules, suspensions, syrups, and elixirs. Inert diluents and carriers for tablets include, for example, calcium carbonate, sodium carbonate, lactose and talc. Tablets may also contain granulating and disintegrating agents such as starch and alginic acid, binding agents such as starch, gelatin and acacia, and lubricating agents such as magnesium stearate, stearic acid and talc. Tablets may be uncoated or may be coated by unknown techniques; e.g., to delay disintegration and absorption. Inert diluents and carriers which may be used in capsules include, for example, calcium carbonate, calcium phosphate and kaolin. Suspensions, syrups and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions and the like. They may also be manufactured in the form of sterile solid compositions which can be dissolved or suspended in sterile injectable medium immediately before use. They may contain suspending or dispersing agents known in the art.

One aspect of the invention herein is directed to therapeutically inhibiting tumor growth in an animal host having a tumor sensitive to the compounds of the instant invention which comprises administering to said host an effective antitumor dose of said compound. It will be appreciated that the actual preferred amount of compound of the instant invention will vary according to the particular compound, the particular composition formulated, the mode of application and the particular situs, host and disease being treated. Many factors that modify the action will be taken into account by those skilled in the art; e.g., age, body weight, sex, diet, time of administration, route of administration, rate of excretion, condition of the host, drug combinations, reaction sensitivities and severities and severity of disease. Administration can be carried out continuously or periodically within the maximum tolerated dose. Optimal application rates for a given set of conditions can be ascertained by those skilled in the art using conventional dosage administration tests in view of the above guidelines.

The following examples are provided in order to more fully illustrate the present invention.

EXAMPLE 1

2′,7-bis′O-(2,2,2-trichloroethoxycarbonyl)-10-deacetyl taxol (12)

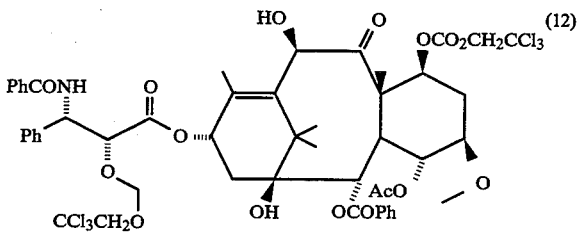

10-Deacetyl taxol (140 mg, 0.173 mmol) in dry dichloromethane (3.5 mL) was treated at 0° C. with pyridine (0.028 mL, 0.346 mmol) and trichloroethyl chloroformate (0.0724 mL, 0.260 mmol). After 1 h at this temperature, the cold bath was removed and the mixture was stirred at room temperature overnight. The solvent was evaporated and the residue chromatographed on silica gel (30–50% ethyl acetate in hexane) to afford 12 as a foam (92.3 mg, 46%). Further elution afforded unreacted starting material (35 mg, 25%). Carbonate 12 had NMR (300 MHz, CDCl$_3$) δ8.14 (d, J=8.5 Hz, 2H) 7.75 (d, J=8.5 Hz, 2H) 7.65-7.35 (m, 11H) 6.94 (exch.d, J=9.3 Hz, 1H) 6.27 (br t, 1H) 6.04 (dd, J=9.3 Hz, J'=2.6 Hz, 1H) 5.71 (d, J=6.9 Hz, 1H) 5.54 (d, J=2.6 Hz, 1H) 5.43-5.37 (m, 2H) 4.96 (d, J=7.9 Hz, 1H) 4.85-4.67 (m, 4H) 4.29 (AB q, 2H) 4.04-4.01 (m, 2H) 2.69-1.80 (m, 14H incl. singlets at 2.58, 1.96, 1.89, 3H each) 1.20 (s, 3H) 1.09 (s, 3H).

High Res. Mass Spectrum: Calcd for C$_{51}$H$_{51}$NO$_{17}$Cl$_6$K (MK+) 1198.0925, found 1198.0949.

EXAMPLE 2

2',7-bis'O-(2,2,2-trichloroethoxycarbonyl)-10-desacetoxy-11,12-dihydrotaxol-10,12(18)-diene (13)

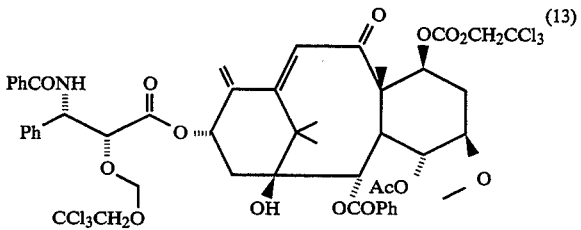

Bis-carbonate 12 (92.3 mg, 0.079 mmol) in dry dichloromethane (2 mL) was treated at room temperature with TFCT (0.0384 mL, 0.238 mmol). The solution was stirred overnight. The solvent was evaporated and the residue purified by column chromatography (25% ethyl acetate in hexane) to afford 13 as a white powder (42.8 mg, 47.3%). NMR (300 MHz, CDCl$_3$) δ8.18 (d, J=8.5 Hz, 2H) 7.69 (d, J=8.5 Hz, 2H) 7.58-7.28 (m, 11H) 6.90 (exch. d, J=9.7 Hz, 1H) 6.31 (s, 1H) 6.25 (br t, 1H) 6.04 (dd, J=9.7 Hz, J'=2.2 Hz, 1H) 5.80 (d, J=7.8 Hz, 1H) 5.51 (d, J=2.2 Hz, 1H) 5.38 (d, J=2.3 Hz, 1H) 5.31 (dd, J=11.0 Hz, J'=7.3 Hz, 1H) 4.99 (d, J=2.3 Hz, 1H) 4.97 (br d, 1H) 4.80-4.65 (m, 4H) 4.30 (AB q, 2H) 3.75 (d, J=7.8 Hz, 1H) 2.60 (m, 1H) 2.55 (s, 3H) 2.16-2.09 (m, 3H) 1.83 (s, 3H) 1.77 (s, 1H) 1.13 (s, 3H) 1.07 (s, 3H).

High Res. Mass Spectrum: Calcd for C$_{51}$H$_{49}$NO$_{16}$Cl$_6$K (MK+) 1180.0820, found 1180.0777.

EXAMPLE 3

10-Desacetoxy-11,12-dihydrotaxol-10,12(18)-diene (14)

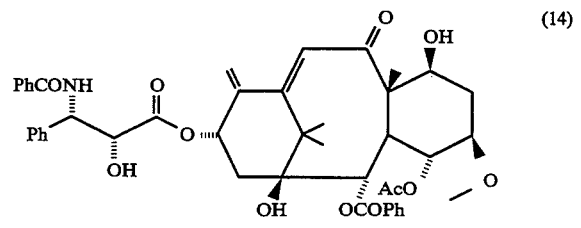

Dienone 13 (180 mg, 0.157 mmol) was dissolved in methanol (3 mL) and treated with acid-washed Zn dust (300 mg, 4.72 mmol). The slurry was refluxed for 20 min, filtered, and the filtrate evaporated. Chromatography of the residue (40-60% ethyl acetate in hexane) gave 14 as a foam (18 mg, 14%), together with its 7-epi isomer (97 mg, 77.7%).

Compound 14 had NMR (300 MHz, CDCl$_3$) δ8.19 (d, J=8.5 Hz, 2H) 7.69 (d, J=8.5 Hz, 2H) 7.59-7.25 (m, 11H) 7.00 (exch. d, J=10.4 Hz, 1H) 6.20 (br t, 1H) 5.96 (s, 1H) 5.83-5.77 (m, 2H) 5.18 (d, J=2.2 Hz, 1H) 4.94 (dd, J=7.2 Hz, J'=2.1 Hz, 1H) 4.79 (d, J=2.2 Hz, 1H) 4.72 (dd, J=4.3 Hz, J'=2.2 Hz, 1H) 4.30 (AB q, 2H) 4.00 (m, 1H) 3.65 (d, J=7.8 Hz, 1H) 3.51 (exch. d, J=4.3 Hz, 1H) 2.60 (m, 1H) 2.40 (s, 3H) 2.30-1.80 (m, 5H) 1.70 (s, 3H) 1.16 (s, 3H) 1.06 (s, 3H).

High Res. Mass Spectrum: Calcd for C$_{45}$H$_{48}$NO$_{12}$ (MH+) 794.3177, found 794.3152.

Alternatively, dienone 13 (39 mg, 0.034 mmol) was dissolved in methanol (0.5 mL) and acetic acid (0.5 mL), and treated with acid-washed zinc dust (66.4 mg, 1.020 mmol). The slurry was heated at 40° C. for 1 h, filtered and the filtrate evaporated. Chromatography of the residue with 60% ethyl acetate/hexane gave 14 as a foam (22 mg, 81%). Spectral data are the same as the previous ones.

EXAMPLE 4

10-Desacetoxytaxol (15)

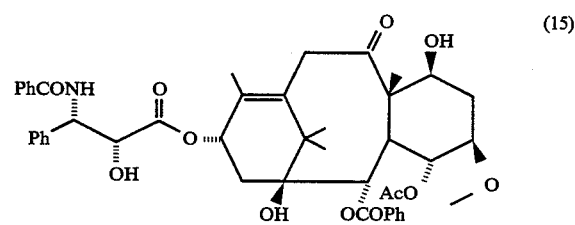

Dienone 14 (22 mg, 0.028 mmol) in ethyl acetate (0.7 mL) was hydrogenated at atmospheric pressure in the presence of palladium on charcoal (10%, 14.7 mg, 0.014 mmol Pd) After 5.5 h at RT, filtration (rinsing with ethyl acetate), evaporation and chromatography (60% ethyl acetate in hexane) gave 10-deoxytaxol 15 (15.0 mg, 68%) as a white foam. NMR (CDCl$_3$) δ8.12(d, J=8.5 Hz, 2H) 7.61 (d, J=8.4 Hz, 2H) 7.60-7.27 (m, 11H) 7.06 (exch. d, J=8.9 Hz, 1H) 6.09 (br t, 1H) 5.78 (dd, J=8.9 Hz, J'=2.6 Hz, 1H) 5.66 (d, J=6.8 Hz, 1H) 4.91 (d, J=7.6 Hz, 1H) 4.76 (dd, J=5.1 Hz, J'=2.6 Hz, 1H) 4.29-4.20 (m, 3H) 4.01 (d, J=6.8 Hz, 1H) 3.75 (d, J=15.8 Hz, 1H) 3.60 (exch. d, J=5.1 Hz, 1H) 3.39 (br d, 1H) 2.60 (m, 1H) 2.34 (s, 3H) 2.34-2.22 (m, 2H) 1.90-1.71 (m, 2H) 1.62 (s, 3H) 1.61 (s, 3H) 1.53 (exch. d, J=7.8 Hz, 1H) 1.14 (s, 3H) 1.12 (s, 3H).

High Res. Mass Spectrum: Calcd for C$_{45}$H$_{50}$NO$_{12}$ (MH+) 796.3333, found 796.3319.

EXAMPLE 5

10-Desacetoxy-7-O-triethylsilyl baccatin III (16)

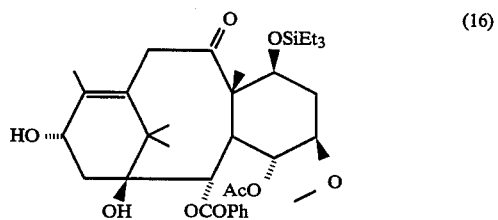

A. 10-desacetyl-7-O-triethylsilyl baccatin III (Compound A)

10-Desacetyl baccatin III (from Taxus baccata, 628.0 mg, 1.150 mmol) was dissolved in dry DMF (6 mL), cooled to 0° C., and treated with imidazole (312.8 mg, 4.595 mmol) and chlorotriethylsilane (0.772 mL, 4.60 mmol). The mixture was stirred at 0° C. for 4 h, then diluted with ethyl acetate (150 mL) and washed exhaustively with water and brine. The organic layer was dried and concentrated. The residue was chromatographed (silica, 50% ethyl acetate in hexane), to afford compound A as a foam (586 mg, 77%). This compound is described by Greene et al. in *J. Am. Chem. Soc.*, 1988, 110, 5917.

B.
10-desacetyl-7-O-triethylsilyl-10-O-(pentafluorophenyloxy)thiocarbonyl baccatin III (Compound B)

Compound A (319 mg, 0.485 mmol) was dissolved in dry THF (5 mL), cooled to −40° C., and treated with n-butyllithium (1.58M in hexanes, 0.384 mL, 0.606 mmol). After 40 min at this temperature, pentafluorophenyl chlorothionoformate (0.086 mL, 0.536 mmol) was added neat by syringe. The reaction mixture was stirred at −20° C. for 90 min, then quenched with saturated ammonium chloride solution, arid extracted with ethyl acetate. The ethyl acetate layer was dried, evaporated and the residue chromatographed (silica, 40% ethyl acetate in hexane) to afford Compound B as a foam (320 mg, 74%). NMR (CDCl$_3$) δ8.09 (d, 2H) 7.56 (t, 1H) 7.44 (m, 2H) 6.78 (s, 1H) 5.64 (d, J=6.9 Hz, 1H) 4.96-4.89 (m, 2H) 4.49 (dd, J=10.2 Hz, J'=6.6 Hz, 1H) 4.12 (AB q, 2H) 3.80 (d, J=6.9 Hz, 1H) 2.55-0.44 (m, 43H). Mass Spectrum: 884 (MH+).

C. 10-desacetoxy-7-O-triethylsilyl baccatin III.

Thionocarbonate (compound B, 119 mg, 0.135 mmol) was dissolved in dry toluene (3 mL) and treated with 2,2'-azobisisobutyronitrile (AIBN, 2 mg). The solution was degassed with dry nitrogen, then tributyltin hydride (0.055 mL, 0.202 mmol) was added and the solution was heated for 1 h (90° C.). Solvent evaporation and chromatography (silica, 40% ethyl acetate in hexane) gave the title product (87 mg, 99%) as a colorless foam. NMR (CDCl$_3$) δ8.07 (d, J=8.2 Hz, 2H) 7.56 (br t, 1H) 7.44 (m, 2H) 5.57 (d, J=6.7 Hz, 1H) 4.92 (d, J=9.3 Hz, 1H) 4.78 (br s, 1H) 4.48 (dd, J=10.4 Hz, J'=6.6 Hz, 1H) 4.09 (AB q, 2H) 4.06 (d, J=6.7 Hz, 1H) 3.74 (d, J=14.8 Hz, 1H) 3.35 (br d, 1H) 2.44 (m, 1H) 2.25 (s, 3H) 2.22-0.45 (m, 42H). Mass spectrum: 642 (MH+).

EXAMPLE 6

10-Deoxytaxotere (17)

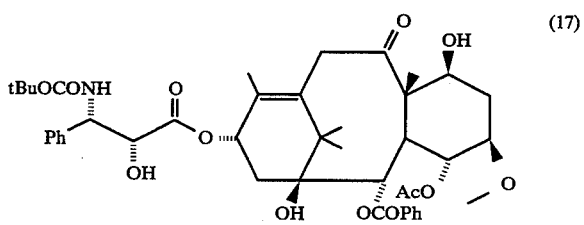

(17)

Compound 16 (100 mg, 0.156 mmol) was placed in a flask under Argon and dissolved in dry THF (1.5 mL). Upon cooling to −40° C., n-butyllithium (1.45M in hexanes, 0.119 mL, 0.170 mmol) was added dropwise, followed by (3R,4S)-1-tert-butoxycarbonyl-4-phenyl-3-triethylsilyloxy-2-azetidinone 94.2 mg, 0.25 mmol) in THF (0.5 mL) over a period of 2 min. The mixture was immediately warmed to 0° C. and stirred for 45 min before quenching with saturated ammonium chloride (3 mL). The mixture was extracted with ethyl acetate, dried, and evaporated. Silica gel chromatography (30% ethyl acetate in hexane ) afforded 2',-7-bis-O-(triethylsilyl)-10-deoxytaxotere as a foam (125 mg. 76%). This compound (100 mg, 0.098 mmol) was immediately dissolved in acetonitrile (2 mL) at −5° C. and treated with hydrochloric acid (0.037 mL, 36%, 12M). The mixture was stirred for 2 h at −5° C., then it was quenched with aqueous bicarbonate, extracted with ethyl acetate, and dried. Evaporation was followed by silica chromatography (75% ethyl acetate in hexane) to afford the title compound as a foam (80.5 mg, 80%). NMR (CDCl$_3$) δ8.10 (d, J=8.2 Hz, 2H) 7.64-7.29 (m, 8H) 6.11 (br t, 1H) 5.68 (d, J=6.9 Hz, 1H) 5.43 (br d, 1H) 5.25 (br d, 1H) 4.93 (d, J=7.7 Hz, 1H) 4.60 (br s, 1H) 4.30-4.18 (m, 3H) 4.02 (d, J=7.7 Hz, 1H) 3.80 (d, J=15.8 Hz, 1H) 3.46-3.40 (m, 2H) 2.62 (m, 1H) 2.35 (s, 3H) 2.35-2.25 (m, 2H) 1.89-1.65 (m, 5H) 1.63 (s, 3H) 1.35 (s, 9H) 1.19 (s, 3H) 1.16 (s, 3H).

EXAMPLE 7

Preparation of (3R,4S)-1-tertbutoxycarbonyl-4-phenyl-3-triethylsilyloxy-2-azetidinone (see Scheme V)

(L)-Threonine methyl ester hydrochloride (1.26 g, 7.44 mmol) in anhydrous dichloromethane (15 mL) was stirred with imidazole (1.01 g, 14.89 mmol) and t-butoxydiphenylsilyl chloride (2.274 g, 7.816 mmol) for 16 h at room temperature. The reaction mixture was partitioned between water and dichloromethane. The organic phase was washed with 5% aqueous sodium bicarbonate and water, dried and concentrated to give 2.88 g of a crude oil, which was used directly in the next step; 1H-NMR (CDCl$_3$) δ7.70-7.25 (m, 10H) 4.44 (m, 1H) 3.62 (s, 3H) 3.31 (d, J=3 Hz, 1H) 2.12 (bs, 2H) 1.3-1.15 (m, 12H).

This oil (548 mg, 1.414 mmol) in anhydrous dichloromethane (10 mL) was treated with benzaldehyde (0.158 mL, 1.55 mmol) at rt overnight in the presence of 4 Å molecular sieves to afford compound of formula XVIIa in situ. Upon cooling the solution containing compound XVIIa to −40° C., triethylamine (0.20 mL, 1.698 mmol) was added, followed by acetoxyacetyl chloride (XVIa) (0.182 mL, 1.698 mmol) over 10 min. The mixture was allowed to reach rt over 4 h and the product was partitioned between dichloromethane and water. The organic phase was further washed with water and brine, dried and concentrated. Silica gel chromatography (being eluted with 1:4 EtOAc/hexane) gave 411 mg of compound XVIIIa as a ca. 10:1 mixture of 3R,4S: 3S,4R diastereomers.

This mixture of diastereomers (245.1 mg, 0.414 mmol) in dry THF (2 mL) was treated with acetic acid (0.15 mL) and tetrabutylammonium fluoride (TBAF, 1M in THF, 1.20 mL). The solution was stirred for 14 h at rt, then partitioned between ethyl acetate and 5% aqueous sodium bicarbonate. The organic phase was dried and concentrated. Flash silica gel chromatography using 1:1 ethyl acetate: hexane as eluant gave 66 mg (Y: 50%) of compound XIXa as a foam in one diastereomer; 1H-NMR (CDCl$_3$) δ6:7.42-7.25 (m, 5H) 5.90 (d, J=4.8 Hz, 1H) 5.09 (d, J=4.8 Hz, 1H) 4.28 (m, 1H) 4.01 (d, J=4.8 Hz, 1H) 3.70 (s, 3H) 1.73 (s, 3H) 1.19 (d, J=6.6 Hz, 3H).

Compound of formula XIXa (9.8 g, 0.0305 mol) in dry dichloromethane (100 mL) was treated at −78° C. with triethylamine (9.40 mL, 0.0671 mol) and methanesulfonyl chloride (MsCl, 3.50 mL, 0.0457 mol). The solution was allowed to reach rt overnight. The reaction mixture was partitioned between water and dichloromethane. The organic layer was washed with 5% aqueous sodium bicarbonate, dilute aqueous HCl, water and brine, and concentrated to afford compound XXa as a crude oily residue. The crude residue (10.0 g) was dissolved in dichloromethane (250 mL) and ozonized at −78° C. until the color of the solution stayed as blue. Addition of methyl sulfide (11 mL) and concentration of the reaction mixture gave compound of formula XXIa (crude).

The compound of formula XXIa was dissolved in THF (150 mL) and treated at −78° C. with hydrazine hydrate (10 mL). After 2 h, the mixture was poured into dilute aqueous HCl and ethyl acetate, and the two phases were separated. The organic phase was washed with more acid, water and brine and concentrated to afford a crude product, which was purified by silica gel chromatography using 1-5% methanol in methylene chloride to yield 4.40 g (Y: 71%) of compound of formula XXIIa; 1H-NMR (CDCl$_3$) δ: 7.38-7.24 (m, 5H) 6.31 (bs, 1H) 5.87 (bm, 1H) 5.04 (d, J=4.8 Hz, 1H) 1.67 (s, 3H).

To a cooled (−5° C.) mixture of 1M aqueous KOH (140 mL) and acetonitrile (100 mL), a solution of compound XXIIa (2.39 g, 11.22 mmol) in acetonitrile (130 mL) was added dropwise. The mixture was stirred at 0° C. for 1 h and diluted with ethyl acetate (300 mL), water (50 mL) and saturated aqueous bicarbonate (50 mL). The organic phase was separated, and the aqueous layer further extracted with ethyl acetate (3×200 mL). The organic phases were combined, dried, filtered and concentrated to give compound of formula XXIIIa (crude), which was recrystallized from hexane/acetone (mp, 184°-6° C.); yield, 1.53 g (Y: 82%).

To azetidinone XXIIIa (580 mg, 3.55 mmol) in dry THF (5.0 mL) was added imidazole (265.5 mg, 3.90 mmol), followed by triethylsilyl chloride (0.654 mL, 3.90 mmol). The mixture was allowed to be stirred for 1 h. Ethyl acetate was added and the organic layer was washed with brine, 10% aqueous HCl and dried. Silica gel chromatography (being eluted with 25% ethyl acetate in hexane) gave 670 mg (Y: 68%) of compound XXIVa as a foam.

To a stirred solution of compound XXIVa (2.20 g, 7.92 mmol) in dry THF (25 mL) was added ethyl diisopropylamine (1.65 mL, 9.51 mmol) at 0° C under argon atmosphere. The solution was stirred for 5 min, then di-tert-butyl carbonate (2.08 g, 9.51 mmol) and 4-dimethylaminopyridine (193.6 mg, 1.58 mmol) were added. The reaction mixture was stirred at 0° C. for 60 min. The reaction was diluted with ethyl acetate (25 mL), and the mixture was washed with brine, 10% aqueous sodium bicarbonate, 10% aqueous HCl, dried over magnesium sulfate, and concentrated to leave an oil. Silica gel flash chromatography (being eluted with 15% ethyl acetate in hexane) gave 2.40 g (Y: 83%) of compound XVa as a white solid; 1H-NMR (CDCl$_3$) δ7.28 (m, 5H) 5.03 (m, 2H) 1.38 (s, 9H) 0.76 (t, J=7.56, 9H) 0.43 (m, 6H).

SCHEME V

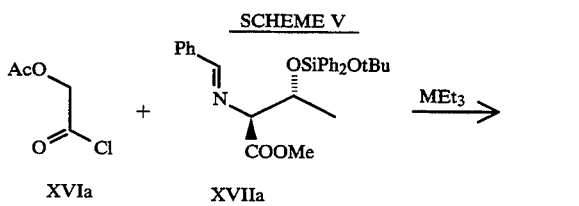

XVIa   XVIIa

-continued
SCHEME V

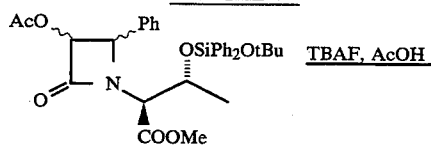

XVIIIa

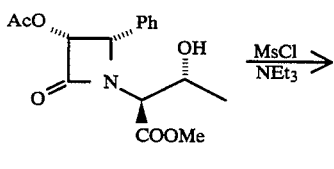

XIXa

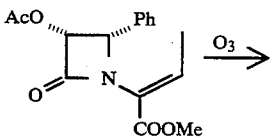

XXa

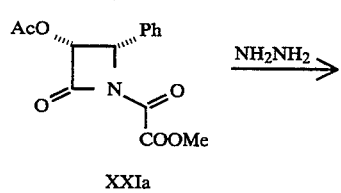

XXIa

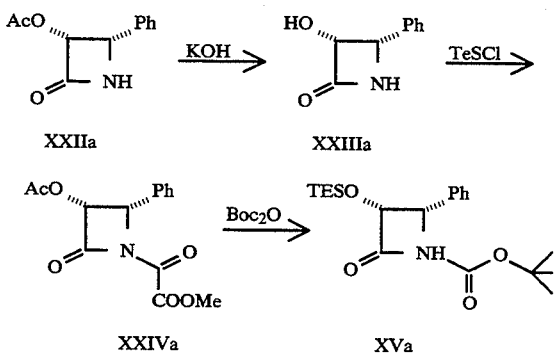

XXIIa   XXIIIa   XXIVa   XVa

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

We claim:

1. A compound of the formula

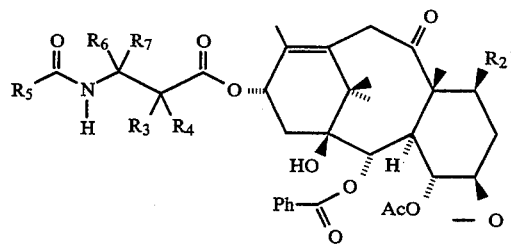

wherein $R_2$ is hydroxy or a protected hydroxy group; $R_3$ and $R_4$ are independently hydrogen, hydroxy, a protected hydroxy group, methyl, —SH, —NH$_2$, or —NR$_8$R$_9$; $R_5$ is $R_{10}$, or —OR$_{10}$; $R_6$ and $R_7$ are independently hydrogen, alkyl, or aryl; $R_8$ and $R_9$ are independently hydrogen, alkyl, alkenyl, alkynyl, or aryl; and $R_{10}$ is alkoxy, alkyl, alkenyl, alkynyl, or aryl.

2. A compound as set forth in claim 1 wherein $R_3$ is hydrogen and $R_4$ is hydroxy or a protected hydroxy group, $R_5$ is phenyl or t-butoxy, $R_6$ is hydrogen, and $R_7$ is phenyl.

3. A compound as set forth in claim 2 wherein $R_5$ is phenyl.

4. A compound as set forth in claim 2 wherein $R_5$ is t-butoxy.

5. A compound as set forth in claim 1 wherein $R_3$ is hydrogen and $R_4$ is —NH$_2$.

6. A compound as set forth in claim 5 wherein $R_5$ is phenyl or t-butoxy.

7. A compound as set forth in claim 1 wherein $R_3$ is methyl, $R_4$ is —SH, $R_6$ is aryl, and $R_7$ is methyl.

8. A compound as set forth in claim 7 wherein $R_5$ is phenyl or t-butoxy.

9. A compound as set forth in claim 1 wherein $R_3$ and $R_6$ are hydrogen; $R_4$ is —NR$_8$R$_9$; $R_5$ is $R_{10}$ and $R_7$ is phenyl.

10. A compound as set forth in claim 9 wherein $R_8$ is hydrogen, $R_9$ is an amine protecting group and $R_{10}$ is t-butoxy.

11. A compound as set forth in claim 1 wherein $R_2$ is hydroxy.

12. A compound as set forth in claim 11 wherein $R_3$ is hydrogen and $R_4$ is hydroxy or a protected hydroxy group, $R_5$ is phenyl or t-butoxy, $R_6$ is hydrogen, and $R_7$ is phenyl.

13. A compound as set forth in claim 11 wherein $R_3$ is hydrogen and $R_4$ is —NH$_2$.

14. A compound as set forth in claim 13 wherein $R_5$ is phenyl or t-butoxy.

15. A compound as set forth in claim 11 wherein $R_3$ is methyl, arid $R_4$ is —SH.

16. A compound as set forth in claim 15 wherein $R_5$ is phenyl or t-butoxy.

17. A compound as set forth in claim 11 wherein $R_3$ and $R_6$ are hydrogen, $R_4$ is —NR$_8$R$_9$, $R_5$ is phenyl or t-butoxy, and $R_7$ is phenyl.

18. A compound as set forth in claim 17 wherein $R_8$ is hydrogen and $R_9$ is an amine protecting group.

19. The compound 10-desacetoxytaxol.

20. The compound 10-deoxytaxotere.

* * * * *

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

In the ABSTRACT, the chemical structure should read

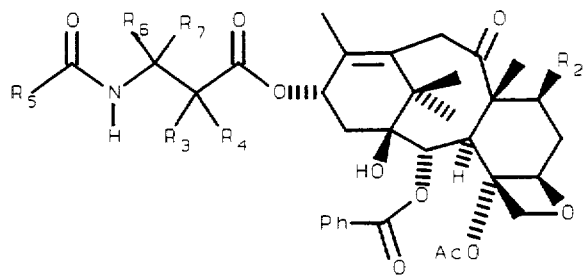

In column 1, line 20, "activity in vivo animal" should read -- activity in in vivo animal --.

In column 1, lines 32-40, the chemical structure should read

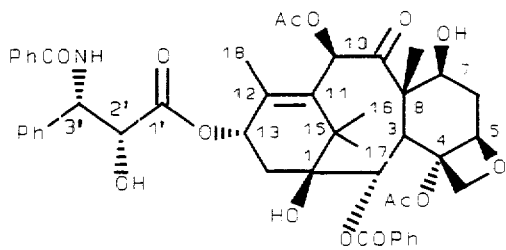

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

In column 1, lines 53-60, the chemical structure should read

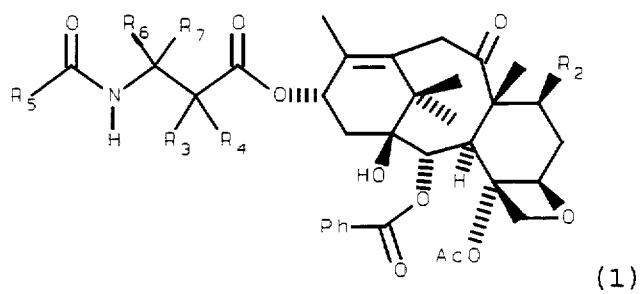

(1)

In column 2, chemical structure (1) should read

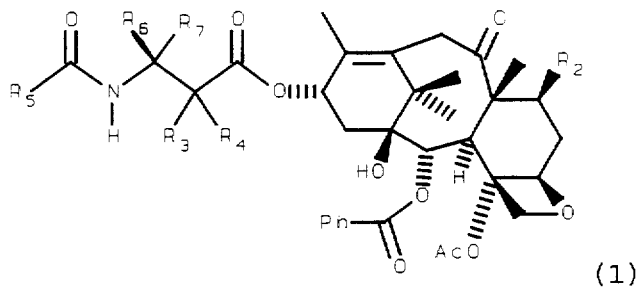

(1)

UNITED STATES PATENT AND TRADEMARK OFFICE
CERTIFICATE OF CORRECTION

PATENT NO. : 5,350,866
DATED : September 27, 1994
INVENTOR(S) : Robert A. Holton, Shu-Hui Chen and Vittorio Farina It is certified that error appears in the above-identified patent and that said Letters Patent is hereby corrected as shown below:

In column 2, chemical structure (2) should read

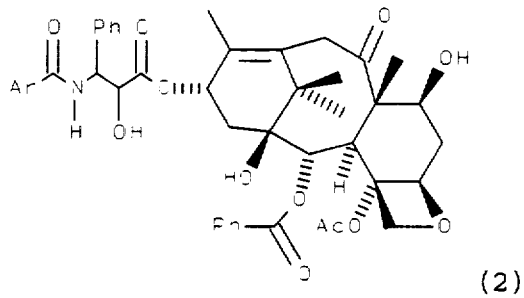

(2)

In column 3, chemical structure (3) should read

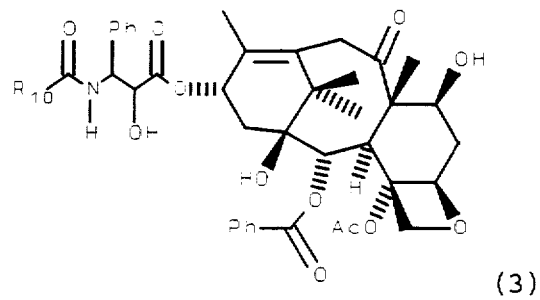

(3)

UNITED STATES PATENT AND TRADEMARK OFFICE
CERTIFICATE OF CORRECTION

PATENT NO. : 5,350,866                         Page 4 of 18
DATED     : September 27, 1994
INVENTOR(S): Robert A. Holton, Shu-Hui Chen
             and Vittorio Farina It is certified that error appears in the above-identified patent and that said Letters Patent is hereby corrected as shown below:

In column 3, chemical structure (4) should read

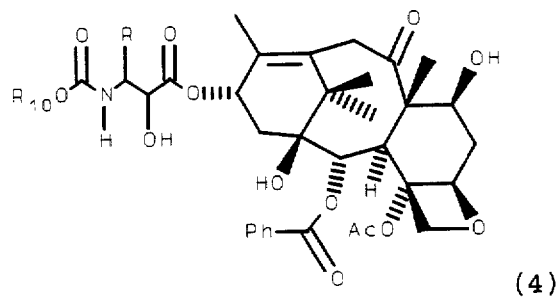

(4)

In column 3, chemical structure (5) should read

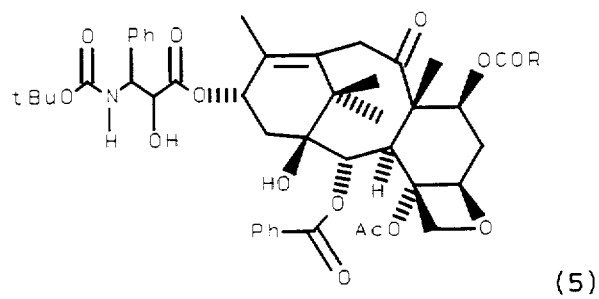

(5)

UNITED STATES PATENT AND TRADEMARK OFFICE
CERTIFICATE OF CORRECTION

PATENT NO. : 5,350,866
DATED : September 27, 1994
INVENTOR(S) : Robert A. Holton, Shu-Hui Chen and Vittorio Farina It is certified that error appears in the above-identified patent and that said Letters Patent is hereby corrected as shown below:

In column 3, chemical structure (6) should read

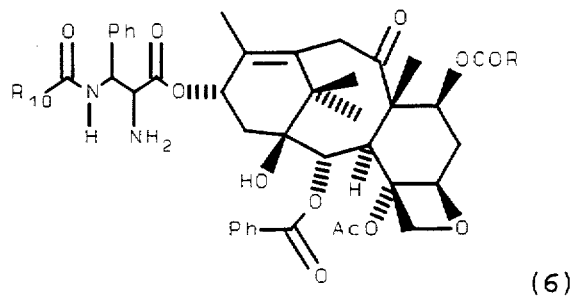

(6)

In column 3, chemical structure (7) should read

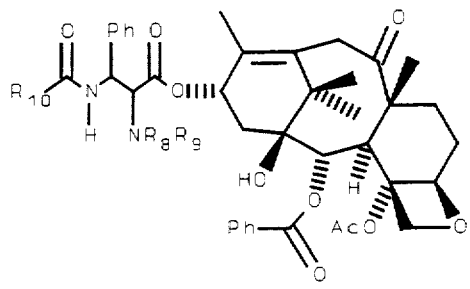

(7)

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

In column 4, chemical structure (8) should read

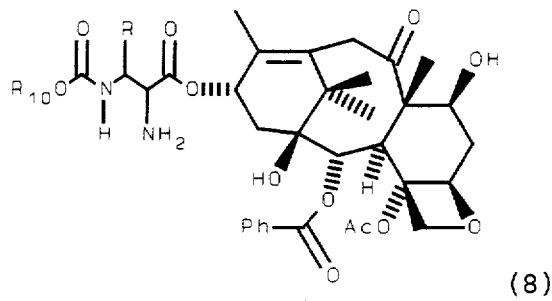

(8)

In column 4, chemical structure (9) should read

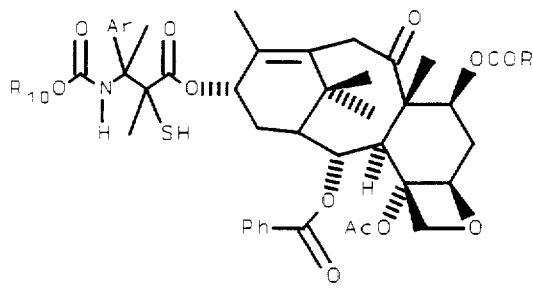

(9)

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

In columns 3 and 4, SCHEME I should read

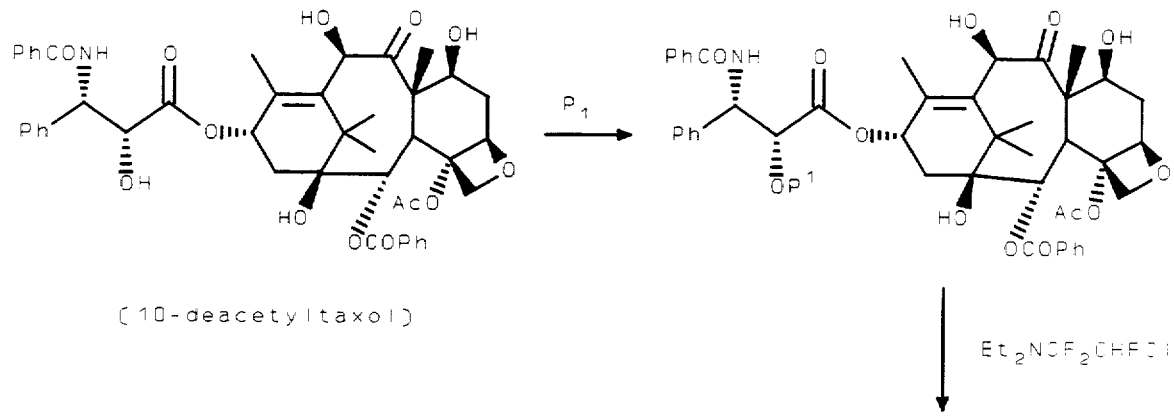

UNITED STATES PATENT AND TRADEMARK OFFICE
CERTIFICATE OF CORRECTION

PATENT NO. : 5,350,866
DATED : September 27, 1994
INVENTOR(S) : Robert A. Holton, Shu-Hui Chen and Vittorio Farina It is certified that error appears in the above-identified patent and that said Letters Patent is hereby corrected as shown below:

In columns 5 and 6, SCHEME I should read

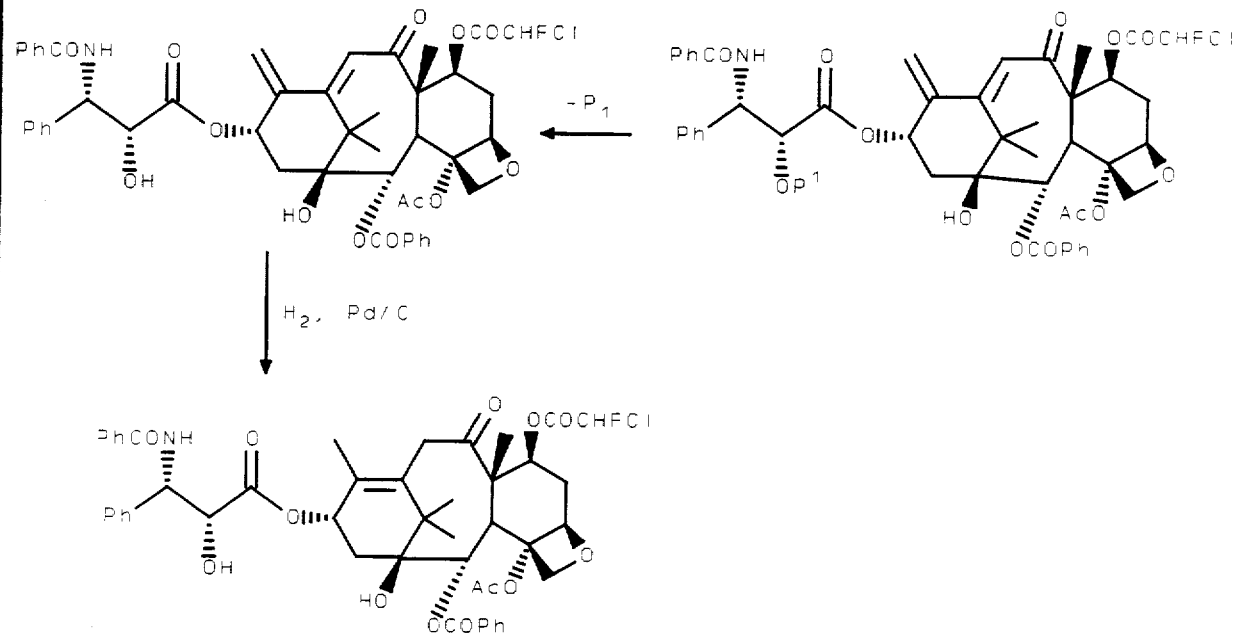

In column 5, line 40, "oil the ring" should read -- on the ring --.

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

In columns 7 and 8, <u>SCHEME II</u> should read

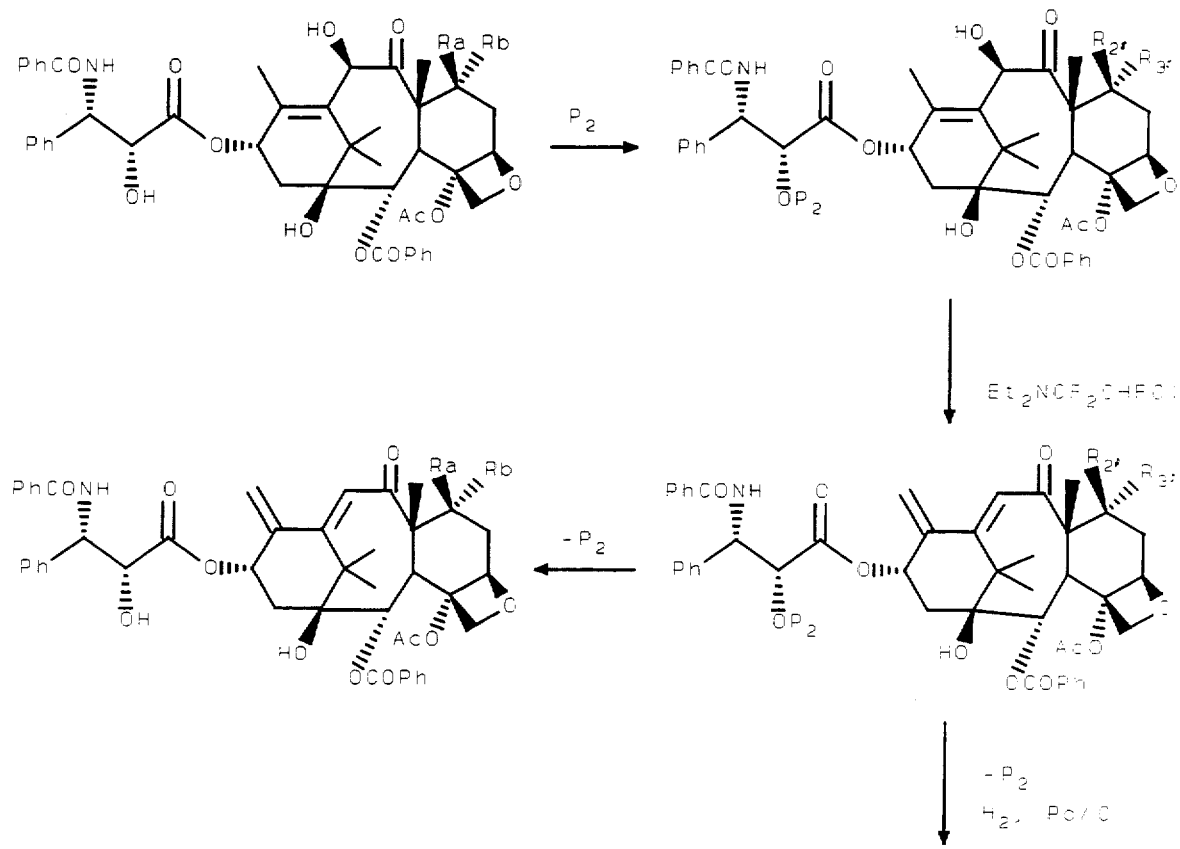

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

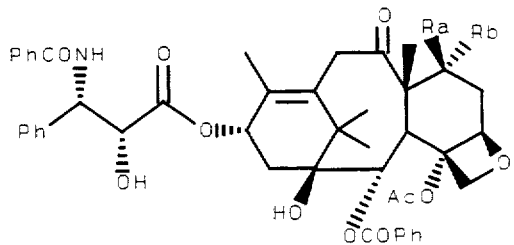

In column 7, line 36, "$R_2$," should read -- $R_{2'}$ --.

In column 7, line 37, "$R_3$," should read -- $R_{3'}$ --.

In column 7, line 38, "$R_2$, is hydrogen, and $R_3$," should read -- $R_{2'}$ is hydrogen, and $R_{3'}$ --.

In column 8, line 38, "of time reaction" should read -- of the reaction --.

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

In column 9, <u>SCHEME III</u> should read

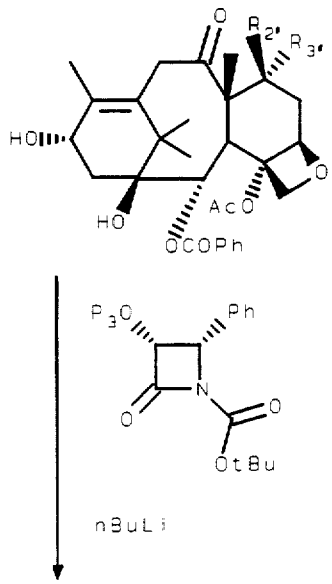

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

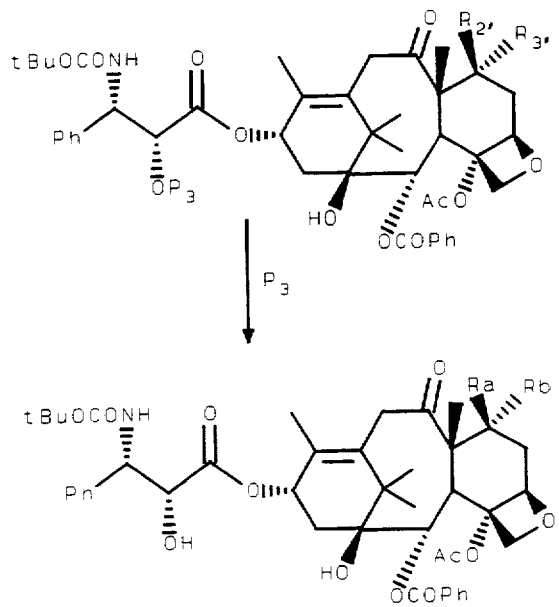

In column 9, line 45, "$R_2$," should read -- $R_{2'}$ --.

In column 9, line 46, "$R_3$," should read -- $R_{3'}$ --.

In column 9, line 47, "$R_2$, is hydrogen, and $R_3$," should read -- $R_{2'}$ is hydrogen, and $R_{3'}$ --.

UNITED STATES PATENT AND TRADEMARK OFFICE
CERTIFICATE OF CORRECTION

PATENT NO. : 5,350,866

DATED : September 27, 1994

INVENTOR(S): Robert A. Holton, Shu-Hui Chen and Vittorio Farina

It is certified that error appears in the above-identified patent and that said Letters Patent is hereby corrected as shown below:

In column 10, <u>SCHEME IV</u> should read

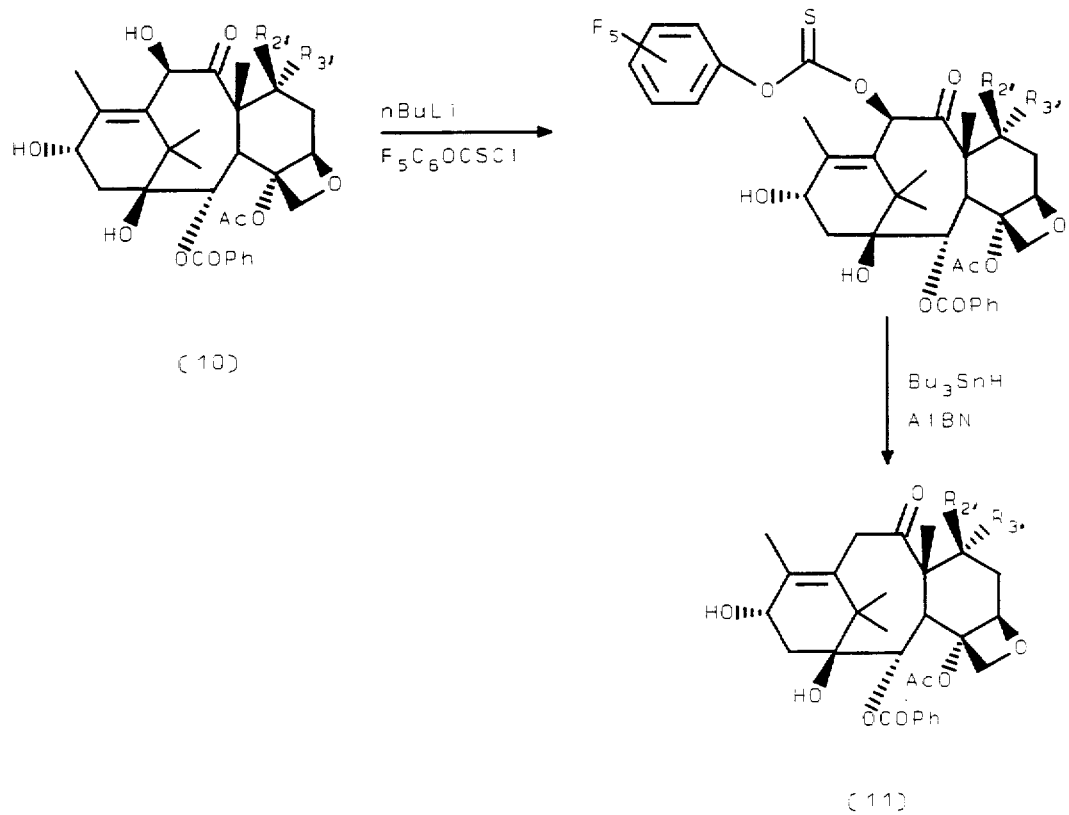

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

In column 10, line 52, "$R_2$, is hydrogen and $R_3$," should read -- $R_{2'}$ is hydrogen and $R_{3'}$ --.

In column 10, line 53, "$R_2$, is protected hydroxy and $R_3$," should read -- $R_{2'}$ is protected hydroxy and $R_{3'}$ --.

In column 12, chemical structure (12) should read

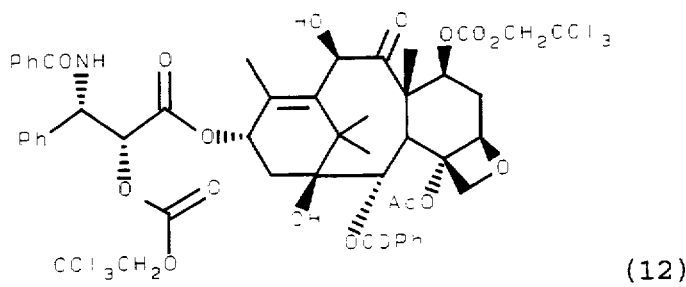

(12)

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

In column 13, chemical structure (13) should read

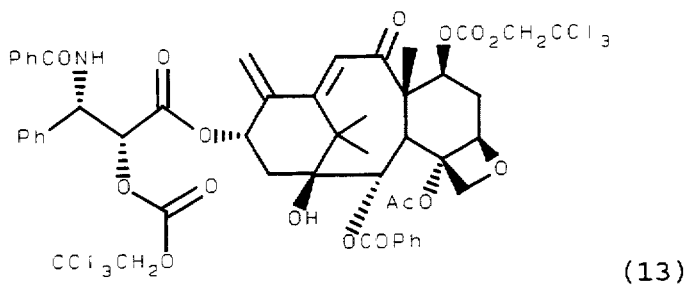

(13)

In column 13, chemical structure (14) should read

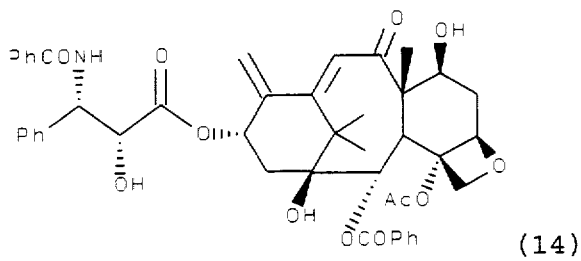

(14)

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

In column 14, chemical structure (15) should read

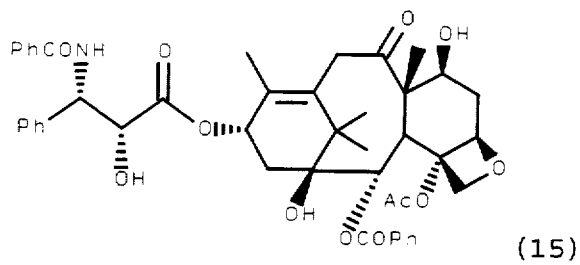

(15)

In column 14, chemical structure (16) should read

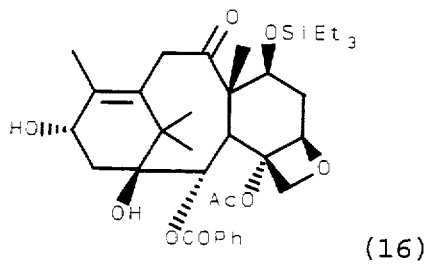

(16)

In column 15, line 18, "solution, arid" should read -- solution, and --.

UNITED STATES PATENT AND TRADEMARK OFFICE
CERTIFICATE OF CORRECTION

PATENT NO. : 5,350,866

DATED : September 27, 1994

INVENTOR(S) : Robert A. Holton, Shu-Hui Chen and Vittorio Farina

It is certified that error appears in the above-identified patent and that said Letters Patent is hereby corrected as shown below:

In column 15, chemical structure (17) should read

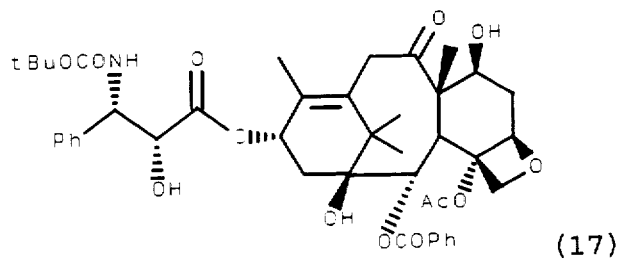

(17)

In column 16, line 32, "δ7.70-7.25" should read -- δ: 7.70-7.25 --.

In column 16, line 59, "δ6:7.42-7.25" should read -- δ: 7.42-7.25 --.

In column 18, <u>SCHEME V</u>, line 35, that portion of the chemical reading "TeSCl" should read -- TESCl --.

UNITED STATES PATENT AND TRADEMARK OFFICE
CERTIFICATE OF CORRECTION

PATENT NO. : 5,350,866
DATED : September 27, 1994
INVENTOR(S) : Robert A. Holton, Shu-Hui Chen and Vittorio Farina It is certified that error appears in the above-identified patent and that said Letters Patent is hereby corrected as shown below:

In column 18, claim 1, lines 60-65 the chemical structure should read

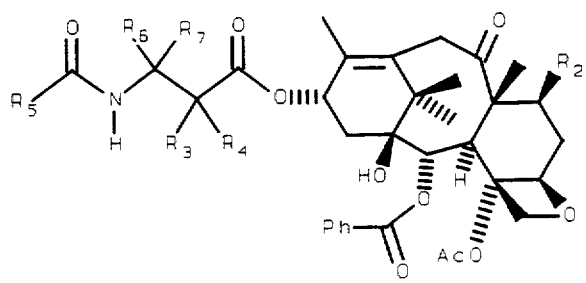

Signed and Sealed this

Eighteenth Day of February, 1997

Attest:

BRUCE LEHMAN

Attesting Officer

Commissioner of Patents and Trademarks